US005489297A

United States Patent [19]
Duran

[11] Patent Number: 5,489,297
[45] Date of Patent: Feb. 6, 1996

[54] BIOPROSTHETIC HEART VALVE WITH ABSORBABLE STENT

[76] Inventor: Carlos M. G. Duran, 1231 Gerald Ave., Missoula, Mont. 59801

[21] Appl. No.: 333,553

[22] Filed: Nov. 2, 1994

Related U.S. Application Data

[60] Continuation-in-part of Ser. No. 34,223, Mar. 19, 1993, Pat. No. 5,376,112, which is a division of Ser. No. 825,913, Jan. 27, 1992, Pat. No. 5,258,021.

[51] Int. Cl.⁶ ........................................................ A61F 2/24
[52] U.S. Cl. ............................................. 623/2; 623/900
[58] Field of Search ........................................ 623/2, 900

[56] References Cited

U.S. PATENT DOCUMENTS

| | | | |
|---|---|---|---|
| 3,463,158 | 8/1969 | Schmitt et al. | 606/154 |
| 3,620,218 | 11/1971 | Schmitt et al. | 606/154 |
| 3,983,581 | 10/1976 | Angell et al. | |
| 4,106,129 | 8/1978 | Carpentier et al. | |
| 4,343,048 | 8/1982 | Ross et al. | |
| 4,451,936 | 6/1984 | Carpentier et al. | |
| 4,680,031 | 7/1987 | Alonso | 623/2 |
| 5,037,434 | 8/1991 | Lane | 623/2 |
| 5,085,629 | 2/1992 | Goldberg et al. | 606/154 |
| 5,258,021 | 11/1993 | Duran | 623/2 |
| 5,306,286 | 4/1994 | Stack et al. | 606/154 |

FOREIGN PATENT DOCUMENTS

| | | |
|---|---|---|
| 874065 | 10/1981 | U.S.S.R. |
| 8300617 | 3/1983 | WIPO |

OTHER PUBLICATIONS

Duran, "A Method for Placing a Total Homologous Aortic Valve in the Subcoronary Position", *The Lancet*, Sep. 8, 1962, pp. 488–489.
Barratt–Boyes, "Homograft aortic valve replacement in aortic incompetence and stenosis", *Thorax*, vol.19, 1964, pp. 131–150.
Sugie, et al., "Clinical Experience with Supported Homograft Heart Valve for Mitral and Aortic Valve Replacement", *The Journal of Thoracic and Cardiovascular Surgery*, vol. 57, No. 4, Apr. 1969, pp. 455–463.
Angell, et al., "Durability of the viable aortic allograft", *The Journal of Thoracic and Cardiovascular Surgery*, vol. 98, No. 1, Jul. 1989, pp. 49–56.
Duran, "Present Status of Reconstructive Surgery of Aortic Valve Disease", *J. Card Surg*, vol. 8, 1993, pp. 443–452.
David, et al., "Aortic Valve Replacement with the Toronto SPV Bioprosthesis", *J. Heart Valve Dis.*, vol. 1, No. 2, Nov. 1992, pp. 244–248.

*Primary Examiner*—Randy C. Shay
*Attorney, Agent, or Firm*—Knobbe, Martens Olson & Bear

[57] ABSTRACT

The invention relates to a bioprosthetic heart valve having leaflets affixed to a substantially absorbable stent. The leaflets can be derived from a biological membrane which is affixed to the absorbable stent. The leaflets can also be derived from a sigmoid valve of human or animal origin, the sigmoid valve being placed inside the absorbable stent and affixed thereto. Methods of treatment using the bioprosthetic heart valve and methods of making the valve are also provided.

7 Claims, 16 Drawing Sheets

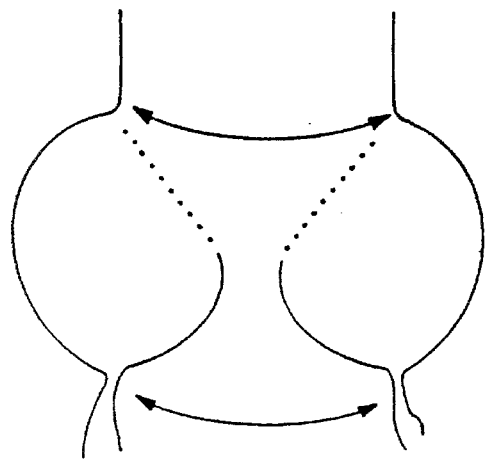
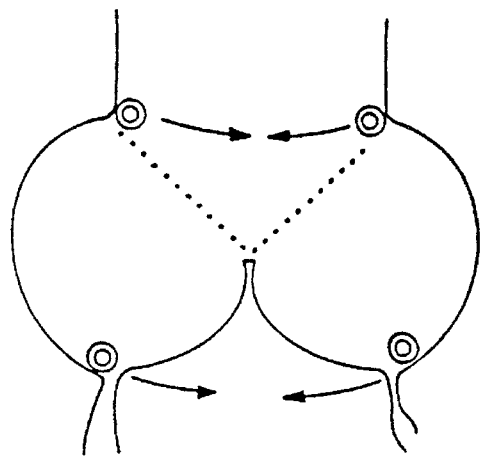
FIG.6A  FIG.6B
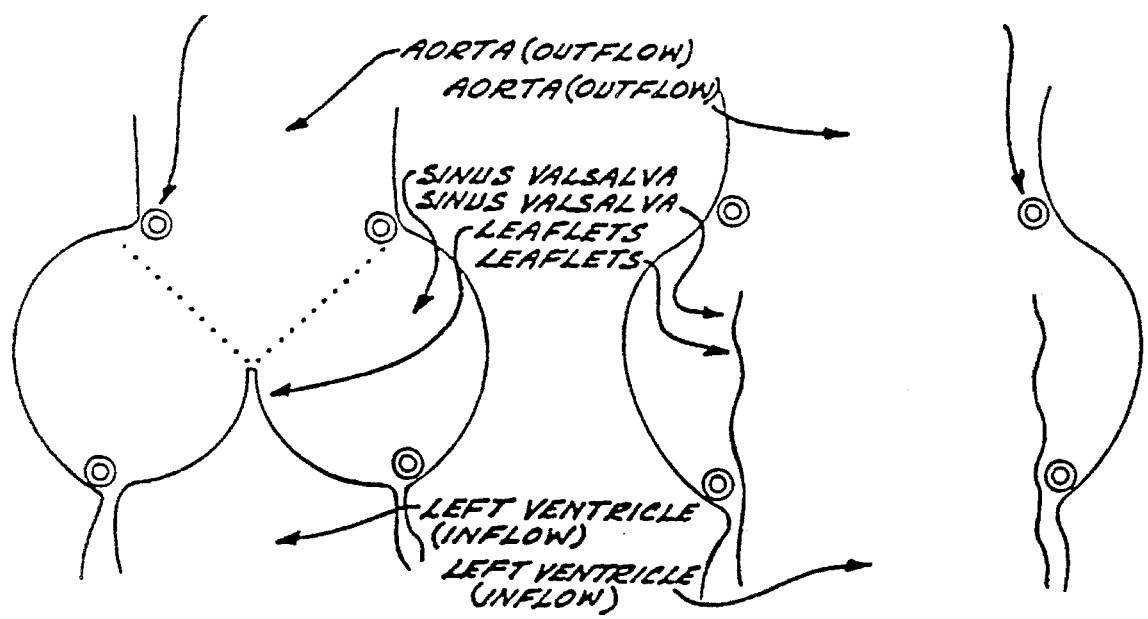
FIG.7A  FIG.7B

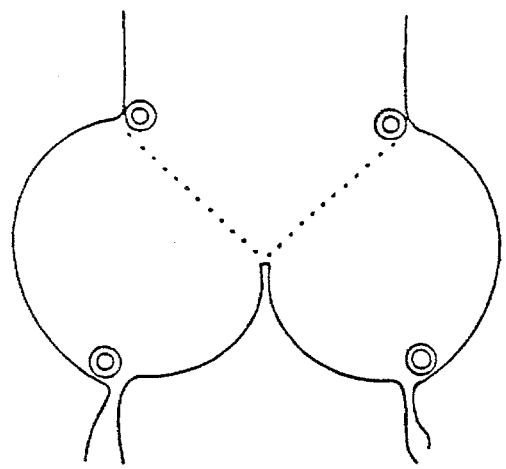
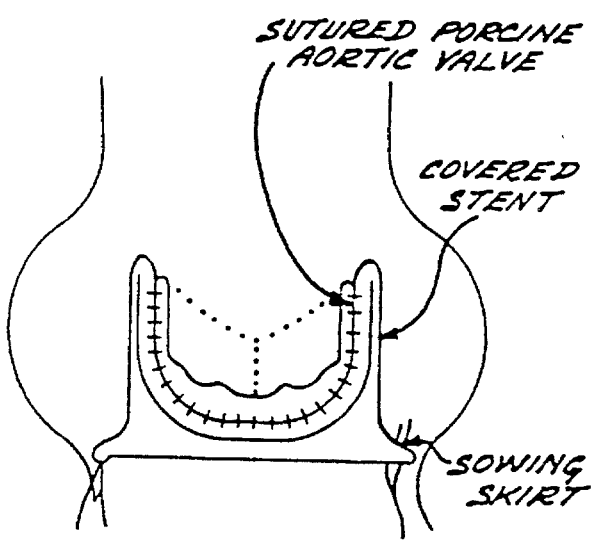
FIG.8A   FIG.8B
FIG.9
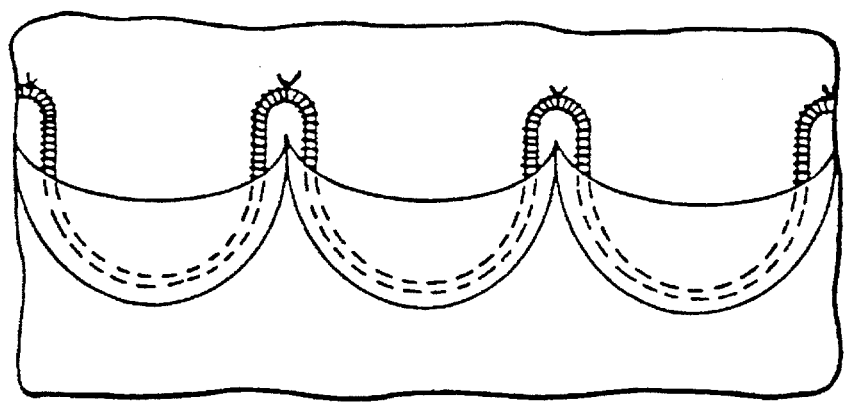

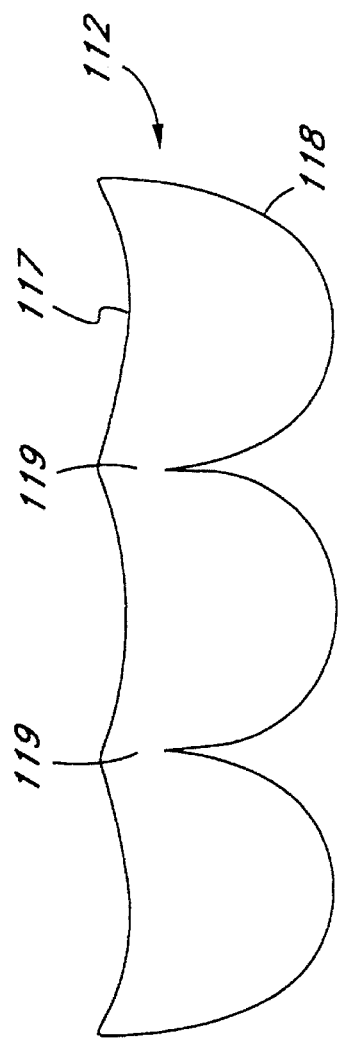
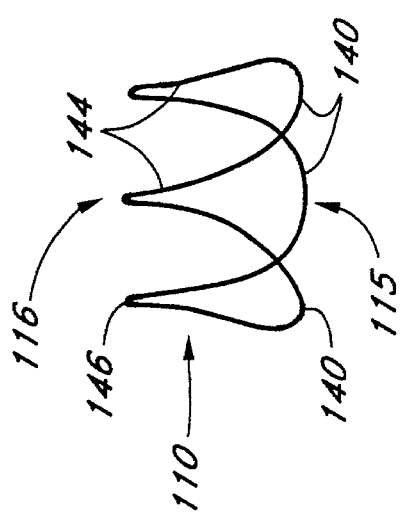
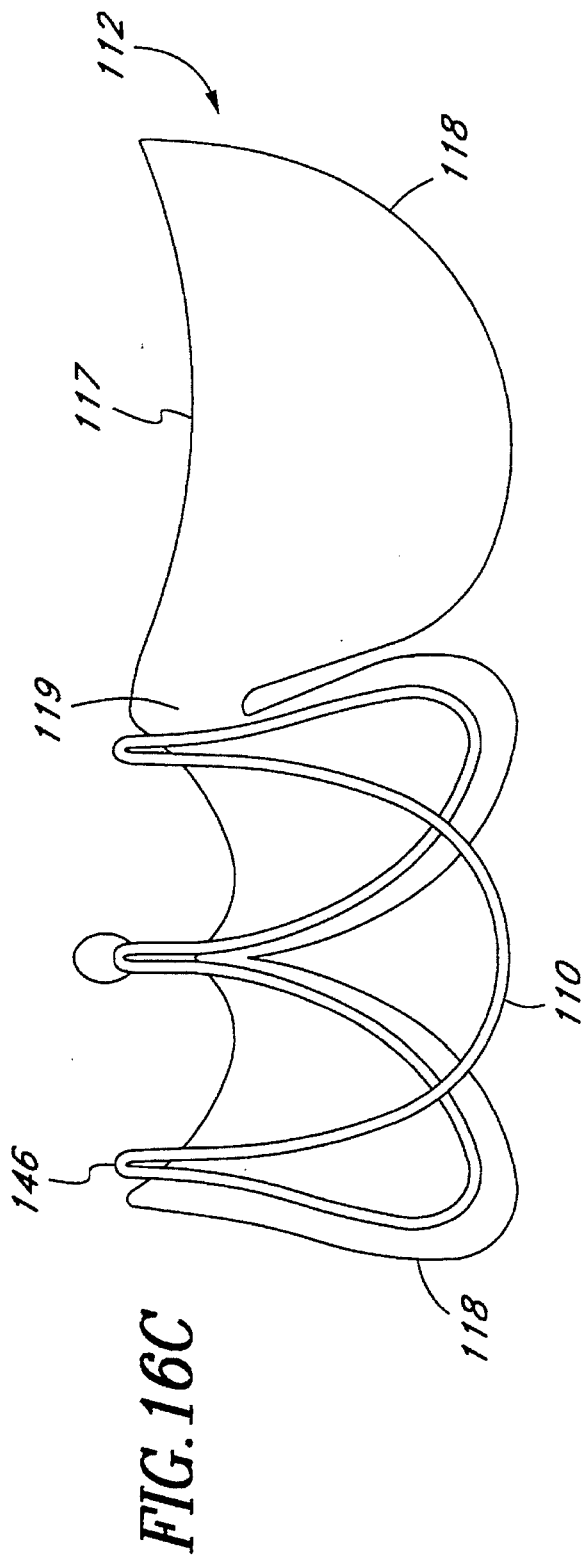
FIG.16A
FIG.16B
FIG.16C

BIOPROSTHETIC HEART VALVE WITH ABSORBABLE STENT

RELATED APPLICATIONS

This application is a continuation-in-part of U.S. application Ser. No. 08/034,223, filed Mar. 19, 1993, now U.S. Pat. No. 5,376,112; which is a divisional application of U.S. application Ser. No. 07/825,913, filed Jan. 27, 1992, now issued as U.S. Pat. No. 5,258,021.

FIELD OF THE INVENTION

The present invention relates to the field of bioprosthetic heart valves and, more particularly, to an absorbable stent for a bioprosthetic heart valve.

BRIEF DESCRIPTION OF THE PRIOR ART

Annuloplasty

Heart valves are deformed by a variety of pathological processes. The vast majority of the patients have their valves replaced by artificial valves which are of two main types: (1) the "mechanical" valves, made of metal or plastic material, and (2) the "tissue" valves, made from animal tissue. These tissue valves use bovine pericardium or a porcine aortic valve which is chemically treated and supported by suturing it to a stent or frame that simplifies its insertion into the annulus of the patient after excision of the diseased aortic or pulmonary valve. These have been termed "bioprosthesis". Several stents for the support of tissue valves have been described and/or patented:

Sugie et al. ("Clinical experience with supported homograff heart valve for mitral and aortic replacement" (1969) J. Thorac. Cardiovasc. Surg. 57:455) describes a support stent that has a circular base with three vertical single posts. The stent is cloth covered so that a tissue aortic valve can be sutured on its inner aspect. The stent cannot be placed at the level of the aortic valve of a patient without previously excising it. Its fiat base in a single plane cannot adapt to the curvatures of the patient's own leaflet insertions and therefore cannot be introduced inside the aortic valve. It is designed for mounting a tissue valve in its interior.

W. W. Angell, U.S. Pat. No. 3,983,581, describes a "stent for a tanned expanded natural tissue valve". The stent comprises a frame whose interior configuration is the anatomical negative of the exterior configuration of a tanned expanded aortic tissue valve. The described device can only be placed on the exterior of an aortic valve and not inside because it would interfere completely with the normal movements of the three leaflets.

A. Carpentier and E. Lane, U.S. Pat. No. 4,451,936, describe "an aortic prosthetic valve for supra-annular implantation comprising a valve body of generally annular configuration and a valve element movable". "The valve body terminates in a generally annular base and a scalloped suture ring . . . which fit the contour of the sinuses of valsalva at the base of the aorta". This device, although it conforms better to the anatomy of the aortic annulus, cannot be placed inside the aortic root without excising the patient's own aortic valve. Its suturing base requires excision of the three leaflets. It is not designed to be used as an annuloplasty device but as a valve replacement.

D. N. Ross and W. J. Hoskin, U.S. Pat. No. 4,343,048, describe a stent for holding in its interior a tissue valve "for the replacement of defective cardiac valves". "The nonviable valve is mounted within". The stent design is such that it cannot be placed within the aortic root without excising the patient's native valve. A feature described to be important in this patent is the flexibility of the stent in order to reduce the stress on the mounted tissue valve.

A. Carpentier and E. Lane, U.S. Pat. No. 4,106,129, describe a new bioprosthetic heart valve that is supported by a wire frame with U-shaped commissural support. This support frame supports a preserved porcine xenograft or xenografts from other species, or an allograft (homograff). This patent does not mention using this support frame for remodelling the diseased annulus of a native aortic valve, nor is this structure adapted for such remodelling. This follows, when the general shape of the wire frame shown and described in this patent is considered. The commissure supports are parallel, the base is fiat and the inflow and outflow orifices are similar. This structure is obviously designed for supporting a tissue valve but not for being implanted inside an aortic root without previously removing the three native leaflets.

All artificial or prosthetic heart valves, whether mechanical or bioprosthesis, although greatly improving the condition of the patient, have some serious drawbacks, namely: thrombogenicity (tendency towards thrombus formation and subsequent detachment with embolization) and limited durability secondary to mechanical or tissue structural failure.

Other complications such as noise, hemolysis (destruction of blood elements), risk of endocarditis (valve infection) and partial dehiscence of the valve also occur. Because of the risk of embolism, the majority of patients who receive artificial heart valves need to take anticoagulative medication for life with the concomitant risk of hemorrhage and necessary change in lifestyle.

Different and more recent developments in the field of cardiac surgery included attempts to surgically repair diseased heart valves. A variety of surgical maneuvers or procedures have been used for this purpose. This type of reconstructive heart valve surgery has been shown to be far superior to valve replacement. References to such reconstructive heart valve surgery can be found, for example, in the following articles: Angell, W. W., Oury, J. H., Shah, P. (1987) A comparison of replacement and reconstruction in patients with mitral regurgitation. J. Thorac. Cardiovasc. Surg. 93:665; and Lawrence, H., Cohn, M. C., Wendy Kowalker, Satinder Bhatia, M.D., Verdi J. DiSesa, M.D., Martin St. John-Sutton, M.D., Richard J. Shemin, M.D., and John J. Collins, Jr., M.D. (1988) Comparative Morbidity of Mitral Valve Repair versus Replacement for Mitral Regurgitation with and without Coronary Artery Disease. Ann. Thorac. Surg. 45:284–290.

Reconstructive surgery, however, is difficult to perform and is not always possible in every patient. Among the variety of reconstructive maneuvers, valve annuloplasty is the most frequently performed in the tricuspid and mitral valves. Valve annuloplasty is an operation which selectively reduces the size of the valve annulus. For this purpose, a number of prosthetic rings have been developed for the atrioventricular valves and are used in an increasing number of patients all over the world. The best known commercially available rings are the Carpentier (distributed by Edwards Labs) and the Duran (distributed by Medtronic Inc.) rings. These are described in the following references: Carpentier, A., Chauvaud, S., Fabiani, J. N., et al. (1980) Reconstructive surgery of mitral incompetence: ten year appraisal. J. Thorac. Cardiovasc. Surg. 79:338; Duran, C. G., Ubago, J. L. (1980) Clinical and hemodynamic performance of a totally flexible prosthetic ring for atrioventricular valve reconstruction (1976) Ann. Thorac. Surg. 22:458–63; and Duran, C. G., Pomar, J. L., Revuelta, J. M., et al. (1980) Conservative operation for mitral insufficiency: critical analysis supported by postoperative hemodynamic studies in 72 patients. J. Thorac. Cardiovasc. Surg. 79:326.

The Carpentier and Duran rings, however, can only be used in the mitral and tricuspid valves. It is surprising that although many stents for supporting aortic tissue valves (bioprosthesis) have been described and patented (vide Supra), none has been even suggested as a possible aortic annuloplasty ring. In fact, their design make it impossible to be used for this purpose. According to the best knowledge of the present inventor, to date there has been no description nor use of a prosthetic ring for annuloplasty of sigmoid valves (aortic or pulmonary).

Furthermore, an important number of patients develop a pathological dilatation (aneurysm) of the ascending aorta which requires its replacement, particularly when a tear occurs (dissection). This dilatation of the aorta also involves the aortic valve annulus, giving rise to an insufficiency due to lack of coaptation of the valve leaflets, which are otherwise normal. The prior art solution to this problem has been the replacement of the ascending aorta with an implanted artificial "valved conduit". Such a "valved conduit" comprises a biocompatible both tube provided with an artificial (mechanical or tissue) valve. Mere replacement of the aorta with a "valveless" artificial conduit while leaving the natural valve in place, is not generally recommended in the art, due to the dilated nature of the valve annulus and due to the danger of further dilation of the unsupported annulus. However, it is also generally recognized in the art that implantation of "valved conduits" raises risks at least of the same complications as other valve replacements.

In view of the foregoing, and to avoid the above noted disadvantages, there is a genuine need in the prior art for a better approach to the treatment of aortic or pulmonary insufficiency. One aspect of the present invention provides such a better approach.

Bioabsorbable Material

Disorders of the cardiac valves cause significant morbidity and mortality. These disorders include degenerative conditions, such as stenosis and insufficiency, as well as congenital malformations.

Treatment of cardiac valvular disorders can require replacement of the defective valve with a prosthetic valve. Prosthetic heart valves are classified as either "mechanical valves" or "bioprosthetic valves". Mechanical valves consist wholly of materials not derived directly from living organisms, and include ball-valve, tilting disc and hinged leaflet designs.

Bioprosthetic valves generally comprise a supporting stent or frame of non-biological material and a plurality of leaflets, usually of biological material. The biological material of the leaflets can be derived from autologous tissues, such as pericardium, fascia lata or cardiac valves, or can be homologous or xenogeneic tissue.

Each type of prosthetic heart valve has advantages and disadvantages. Mechanical heart valves are durable and can be attached directly to the site of the natural valve, but they carry a significant risk of thrombus formation with secondary complications. Chronic anticoagulation therapy decreases the incidence of thrombotic related events but this therapy itself causes hemorrhage is some patients.

Bioprosthetic valves, by comparison, are more prone to ruptures than mechanical valves and the biological tissue portion has a significant rate of calcification which can lead to secondary stenosis or insufficiency. However, bioprosthetic heart valves are associated with fewer thrombotic complications than are mechanical valves. This decreased risk obviates the need for chronic anticoagulation therapy.

Bioprosthetic valves generally require a stent or frame in order to be implanted at the site of the natural valve because stentless bioprosthetic valves are technically difficult to implant. Further, a stent or frame is used to preserve the functional configuration of the valve over time.

A number of stents or flames have been developed for bioprosthetic valves. The following patents disclose some of the stents or flames.

U.S. Pat. No. 3,983,581—10/1976, Angell, et al.
U.S. Pat. No. 4,106,129—8/1978, Carpentier, et al.
U.S. Pat. No. 4,343,048—8/1982, Ross, et al.
U.S. Pat. No. 4,680,031—7/1987, Alonso
U.S. Pat. No. 5,037,434—7/1991, Lane There are a number of disadvantages to the currently used stents or flames for bioprosthetic heart valves. First, suturing leaflets made of biological tissue, such as pericardium, to a frame places stress on the edges of the biological tissue and leads to a significant incidence of failure over time. Further, the stress associated with the junction between the stent or frame and the biological portion of the valve appears to be involved in calcific degeneration of the valves.

Attempts to circumvent these problems have included clamping and gluing the biological tissue to the frame, instead of suturing. Clamping, particularly, distributes the stress over a larger area of the biological tissue, thereby reducing long term damage. Also, integrally molded polymer leaflets have been developed.

The currently available designs, however, do not obviate the problems of long term failure and secondary calcification. Thus, there remains a need for an improved stent or frame for a bioprosthetic heart valve. Ideally, the frame or stent advantageously combines the ease of surgical implantation and maintenance of the correct valve geometry like a stented valve, with the increased durability of a stentless valve. The present invention provides a bioprosthetic heart valve stent with these advantageous properties.

SUMMARY OF THE INVENTION

In a first aspect of the invention, there is provided a bioprosthetic heart valve. The bioprosthetic heart valve includes a stent which defines a blood flow path. The stent is formed at least partially of substantially bioabsorbable material. The stent can be configured in the form of a closed filament having an inflow and an outflow end. In this configuration of the stent, the filament has a plurality of convexities oriented toward the inflow end and a plurality of peaks oriented toward the outflow end. The bioprosthetic heart valve also has a plurality of leaflets having an outer edge and an inner edge. The inner edges of the leaflets are affixed to the stent while the outer edges are adapted to come into contact with each other to close the blood flow path defined by the stent. The leaflets can be derived from biological material, such as pericardium, pleura, peritoneum, fascia lata, or any combination of the foregoing. The biological material of the leaflets can also be derived from xenogeneic tissue, homologous tissue, autologous tissue, or any combination of the foregoing. In one embodiment, the biological material of the leaflets includes a substantial portion of a human cadaveric heart valve. In another embodiment, the biological material of the leaflets includes a substantial portion of a xenogeneic animal heart valve.

A second aspect of the invention relates to a method of treating a mammal having a diseased heart valve. The method includes providing a bioprosthetic heart valve. The bioprosthetic heart valve includes a stent formed at least partially of substantially bioabsorbable material. The bioprosthetic heart valve also includes leaflets of biological material affixed to the stent. The method also includes removing a diseased heart valve from the mammal so that the bioprosthetic head valve can be implanted at the site from which the diseased heart valve was excised. The implanting step of this method can be accomplished by affixing the leaflets to a vascular structure in the mammal. The leaflets of the bioprosthetic heart valve can also have a vessel wall remnant affixed thereto, in which case the implanting step includes using the vessel wall remnant to affix the leaflets to the vascular structure of the mammal. After the bioprosthetic heart valve is implanted, the stent can be substantially absorbed while the leaflets remain in situ.

A third aspect of the invention relates to a method of making a bioprosthetic heart valve. The method includes providing a stent formed at least partially of substantially bioabsorbable material. The method also includes harvesting biological material and shaping the biological material into a leaflet having an inner edge and an outer edge. The inner edge of the leaflet is affixed to the stent to form the bioprosthetic heart valve.

The present invention may be best understood, together with further objects, features and advantages thereof, by reference to the following description, taken in connection with the accompanying drawings.

BRIEF DESCRIPTION OF THE DRAWING

FIGS. 6A and 6B are schematic views of the patient's aortic valve before and after annuloplasty with the "Sigmoid Annuloplasty Ring".

FIGS. 7A and 7B are schematic views of the patient's aortic root during systole and diastole, respectively, after implantation of the "Sigmoid Annuloplasty Ring".

FIG. 8 is a schematic view of the patient's aortic root after ring annuloplasty (A) compared with after bioprosthesis replacement (B).

FIG. 9 is a schematic depiction of an opened sigmoid (aortic or pulmonary) valve (human or animal) showing the three native tissue leaflets and the annuloplasty ring (stent) of the present invention, placed inside the vessel without interference with the three normal leaflets and held to the arterial wall by a continuous suture.

FIGS. 16A-E provide a general depiction of the shape of the absorbable stent and the mounting of a single strip membrane so as to construct an eventually stentless bioprosthesis.

DESCRIPTION OF THE PREFERRED EMBODIMENTS

The following specification taken in conjunction with the drawings, sets forth the preferred embodiments of the present invention. The embodiments of the invention disclosed herein include the best modes contemplated by the inventor for carrying out the present invention. It should be understood that various modifications can be accomplished within the parameters of the present invention.

Annuloplasty

Figure 1:
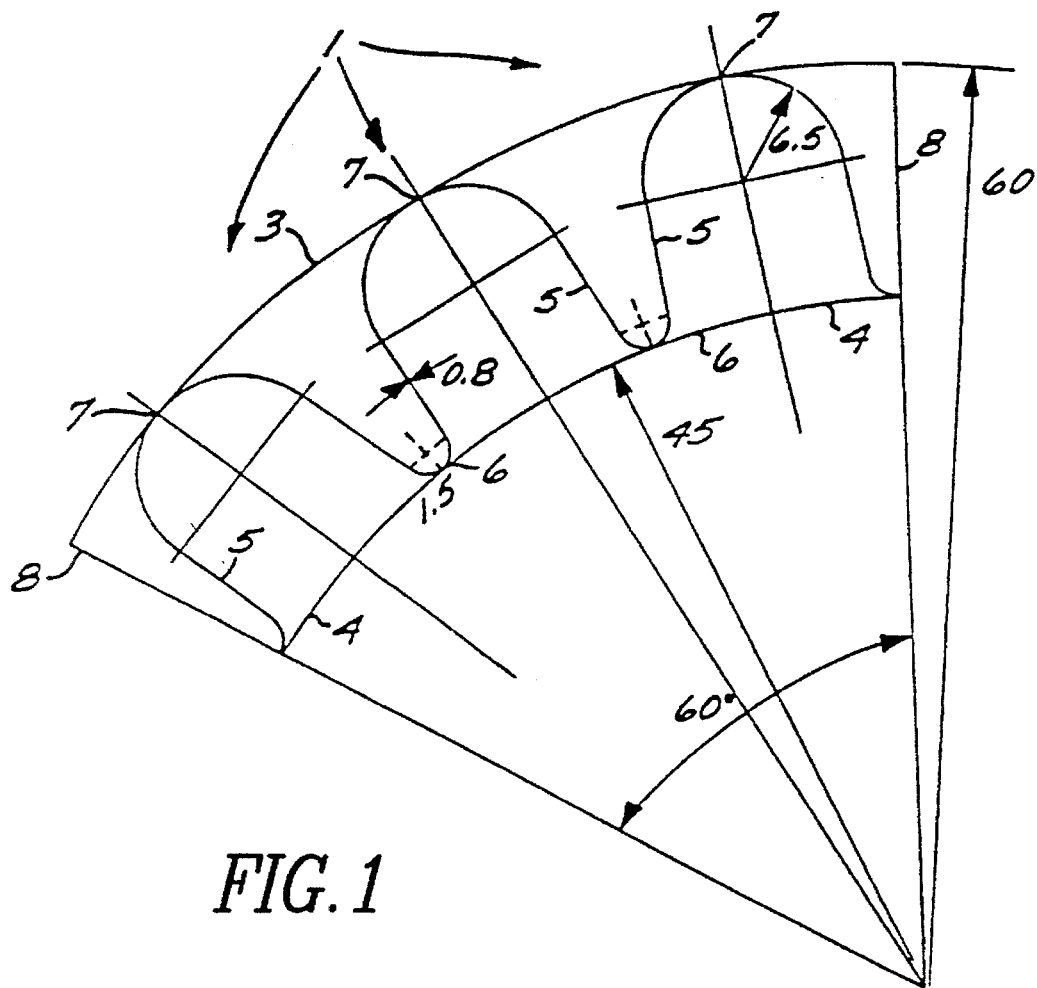
FIG. 1 is a lateral view of the preferred embodiment of the solid stent of the present invention, showing the stent as a fiat pattern.
Figure 2:
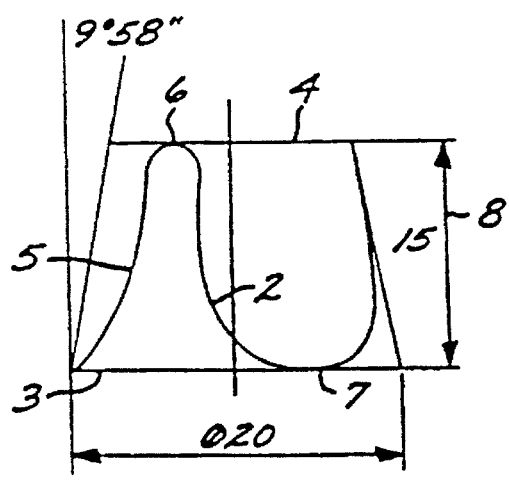
FIG. 2 is a lateral view of the preferred embodiment of the solid stent, showing the relationship of its height to diameter and the difference between the "inflow" and "outflow" diameters.
Figure 3:
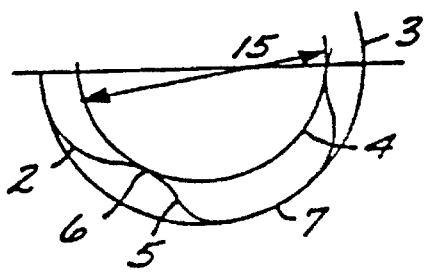
FIG. 3 is a top view of the preferred embodiment of the solid stent, showing again the difference between the inflow (outer) and outflow (inner) diameters.

Referring now to the drawing figures, and particularly to FIGS. 1–3, the preferred embodiment of the sigmoid valve annuloplasty ring 1 of the present invention is disclosed. It should be noted at the outset that although the ensuing description is primarily directed to the use of the annuloplasty ring 1 in the aortic valve area, the invention is not so limited. Rather, the annuloplasty ring 1 can be also applied to the other sigmoid valve of the human (or animal) anatomy, namely, to the pulmonary valve.

Referring now specifically to FIG. 1, an important feature of the present invention is the configuration or shape of the stent of the annuloplasty ring 1. Specifically, the novel stent 1 of the invention has a shape adapted to follow the contour of the normal sigmoid valve. The stent 1 in the first preferred embodiment is constructed from a single solid piece of biocompatible metal. A preferred metal for the stent is titanium or titanium alloy, normally used for implantation. This alloy has very good properties for the present purpose, as well as combining strength with lightness, it is biocompatible.

Biocompatible nonabsorbable plastic materials can also be used for the stent, although they would probably need to be thicker than metal, in order to have sufficient strength. Another alternative is the use of biocompatible polymers that are reabsorbed by the organism after a certain time after their implantation.

The sold single piece 2 of the first preferred embodiment of the stent 1 is shaped into the herein described configuration, which is depicted in FIGS. 1, 2, 3 and 4.

the stent 1 has a circular appearance of configuration, when it is viewed from the top or bottom, as is shown on FIG. 3. The "circle" 3 on the bottom represents a wider "inflow" orifice, and the "circle" 4 on the top represent a smaller "outflow" orifice. Thus, as is shown in the drawing figures (principally FIGS. 1–4), the stent forms a "convoluted ring" having three substantially sinusoidal struts 5 which project upwardly from the base "diameter" of the convoluted ring. The ring itself is curved both at its lower (inflow) and upper (outflow) ends so that if placed on a horizontal plane it would only make contact in three points. Each strut has a separate descending and an ascending portion 5 which are generally nonparallel relative to one another. These ascending and descending limbs 5 are joined by smooth curved upper 6 and lower 7 portions (FIGS. 1, 2, 3, 4). These joining parts are curved both in the frontal or lateral and axial view (FIGS. 1, 2 and 3). The angle formed by the ascending and descending limbs 5 in relation to the vertical is substantially 10° (FIGS. 1 and 2).

Figure 4:
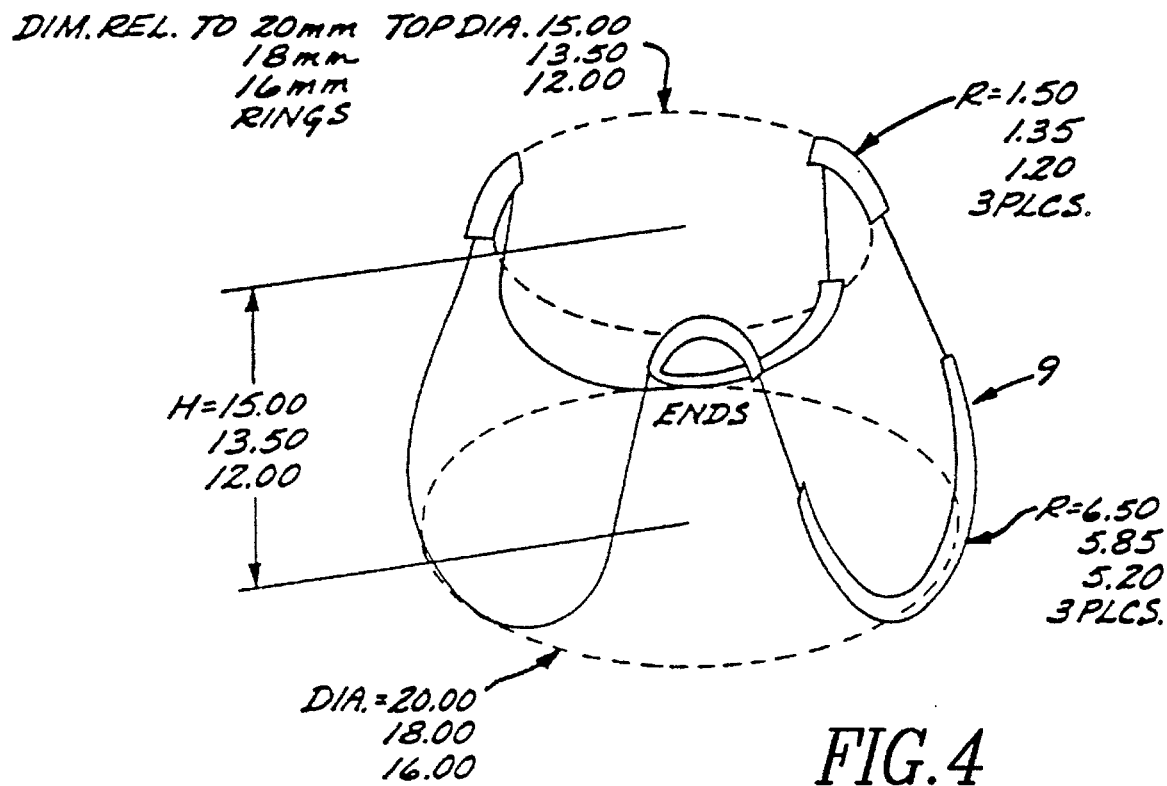
FIG. 4 is a perspective view of the preferred embodiment of the stent with the relative measurements of each of its parts in relation to the inflow diameter.

Proportions between the height and width of the stent can be varied, for as long as the stent meets its stated objective to reduce the circumference of a diseased annulus to its substantially normal size, and to permit the native valve leaflets to seal against each other as shown in FIG. 4. An exemplary stent 1 depicted in the drawings has the following dimensions: the diameter of the lower "inflow" orifice circle 3 is 20 mm, the diameter of the upper "outflow" orifice circle 4 is 15 mm, the total height 8 of the stent 1 is 15 mm, and the radii of the "turns" of the stent to form the sinusoidal struts are 1.5 mm for the upper 6 and 6.5 mm for the lower 7 curve. Those skilled in the art will recognize that the foregoing dimensions and proportions can be varied within certain limits; nevertheless, preferably the proportions described above and shown in the drawings are maintained. Limits of the dimensions are to be construed in this regard to be such that the stent of the invention must approximate the natural shape of the normal heart valve. With respect to the actual "inflow" and "outflow" diameters of the stent 1 (as opposed to relative proportions), the stent 1 of the invention must be manufactured in different sizes to accommodate the different sizes of the human sigmoid valve, which itself varies for each individual. An approximate range of such sizes is between 15 to 35 mm for the inflow diameters. Dimensions of a number of examples of stents constructed in accordance with the invention to fit different patients, are given in FIG. 4.

For implantation, the stent 1 is covered with biocompatible cloth. In this regard, biocompatible cloth comprises a fabric mesh of biocompatible material, preferable polyester (polyacetate) fabric. The use of such biocompatible fabric mesh to enclose various plastic or metal members which are subsequently surgically implanted in the human body is well known in the art. As is further known, after implantation into the human body, an ingrowth of fibrous tissue usually forms in the interstitial spaces of the fabric, and endothelial cells cover the fabric to provide a nonthrombogenic autologous surface. Therefore, at least sometime after the implantation, the cloth covered metal or plastic member no longer causes coagulation of blood and presents no significant danger of thrombus formation when implanted in the heart.

Figure 5:
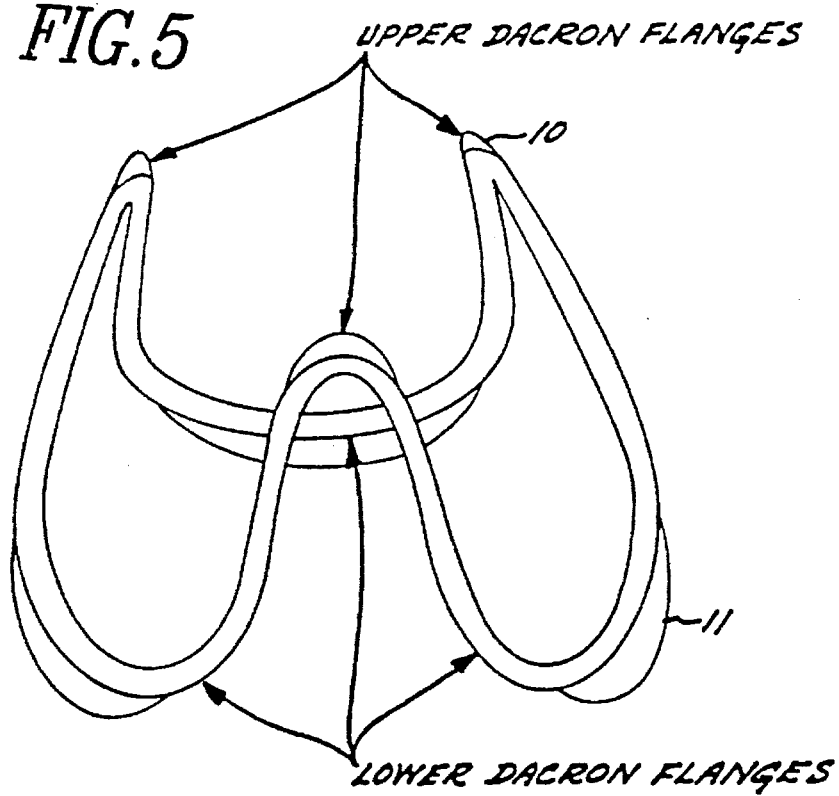
FIG. 5 is a perspective view of the preferred embodiment with the cloth covering showing the cloth flanges for holding the anchoring sutures.

In accordance with the present invention, the stent 1 is totally covered with this thin fabric, preferably of approximately 0.3 mm thickness, so that there are no plastic or metal surfaces exposed to come into contact with tissue or blood flow. The biocompatible cloth cover of the stent is best illustrated in FIGS. 4 and 5. Different modes of covering the stent are: (a) either by a single layer of cloth 9 in FIG. 4 that fits exactly the shape, thickness and dimensions of the stent, or (b) by doubling the cloth at the lowest and highest points of curvature of the sinusoids of the stent (10 and 11 in FIG. 5). The object of these flanges 10 and 11 is to simplify the identification by the surgeon of these points where the initial anchoring sutures must be placed. Six such sutures placed at the highest 10 and lowest 11 curvatures of the ring must coincide with a point above each commissure and at the lowest point of each sinus of Valsalva of the patient. It is important to avoid contact of the ring with any of the patient's own leaflets, as depicted in FIGS. 6 and 7 which show the mechanism of action of the present invention (FIG. 7) and how it does not interfere with the movements of the patient's sigmoid valve leaflets during the cardiac cycle (FIG. 8). Closure of the sigmoid valve returns to normal by leaflet apposition because of the reduction in the valve annulus induced by the ring. Thus, patients have an implant of the fabric covered stent 1 of the present invention may be gradually weaned from anti-thrombogenic medication, at least sometime after the implantation. To emphasize, this is because, as soon as the cloth covered prosthesis (annuloplasty ring)is covered by human tissues, there are no exposed thrombogenic surfaces in the prosthesis and no further danger of embolus formation.

It is emphasized in connection with the annuloplasty ring or prosthesis of the invention, that it is not intended to serve as a heart valve prosthesis, nor as a stent for heart valve prosthesis. Rather, the present invention is an annuloplasty ring, a prosthesis which is to be implanted into the heart to function together with the native heart valve.

Figure 10:
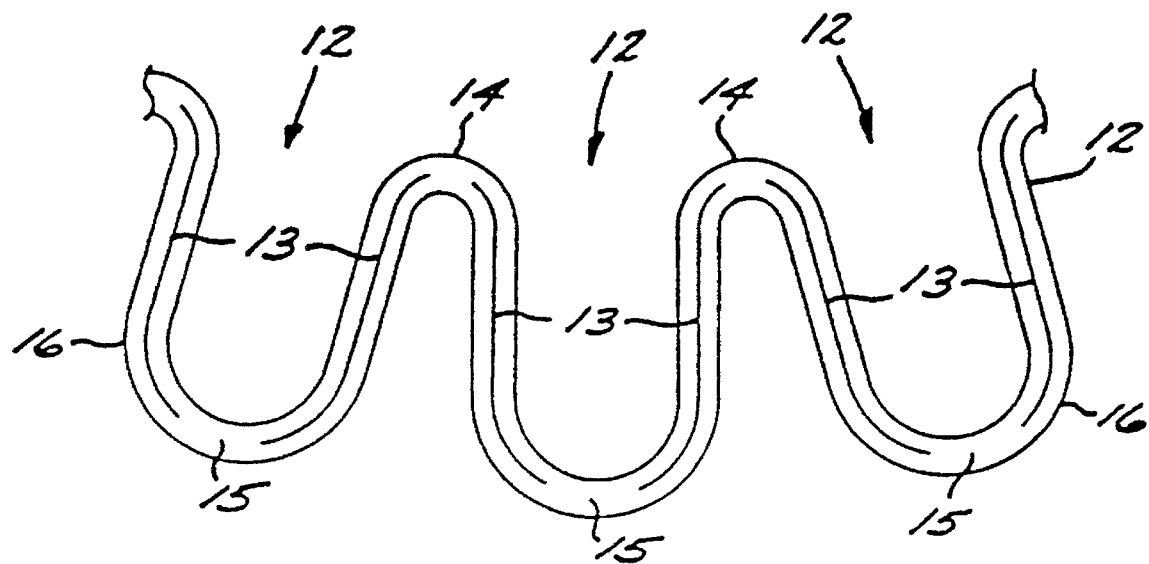
FIG. 10 is a lateral view of the second preferred embodiment of the stent of the present invention showing the stent in a fiat pattern with the solid struts joined by the cloth cover.
Figure 11:
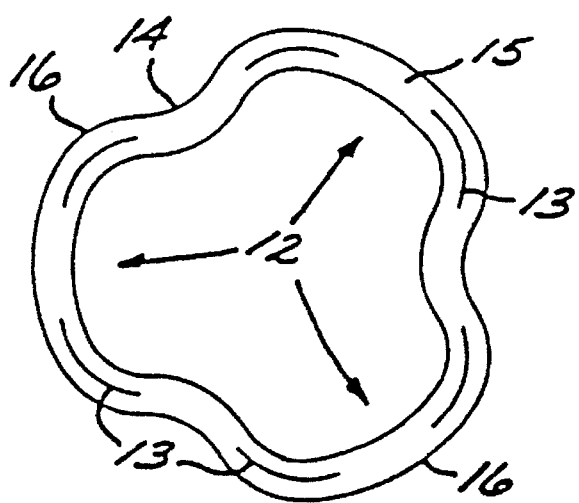
FIG. 11 is a top view of the second preferred embodiment of the stent showing the solid struts joined by the cloth cover.

The second preferred embodiment of the sigmoid ring 12 is depicted in FIGS. 10 and 11. In this preferred embodiment, the struts 13 are made of solid material with the same configuration as in the first preferred embodiment (5 in FIGS. 1, 2, 3 and 4). However, these struts 13 are interrupted at the level of the highest curvature 14 and lowest curvature 15 corresponding to 6 and 7 in the first preferred embodiment. Continuity of the stent 12 is re-established by the cloth covering 16 of the stent 12 which fits exactly over the ascending and descending solid limbs 13. In this second preferred embodiment, there is no need for constructing cloth flanges for simplifying the suturing of the ring as shown at 10 and 11 in FIG. 5 of the first embodiment. In this second embodiment, the anchoring sutures of the sigmoid annuloplasty ring can be passed without difficulty through the cloth at 14 and 15.

Figure 12:
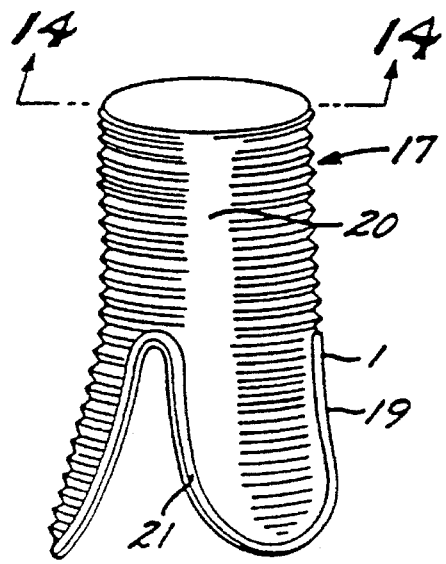
FIG. 12 is a perspective view of a first preferred embodiment of an aortic valveless conduit in accordance with the present invention, and incorporating the stent of the present invention.
Figure 14:
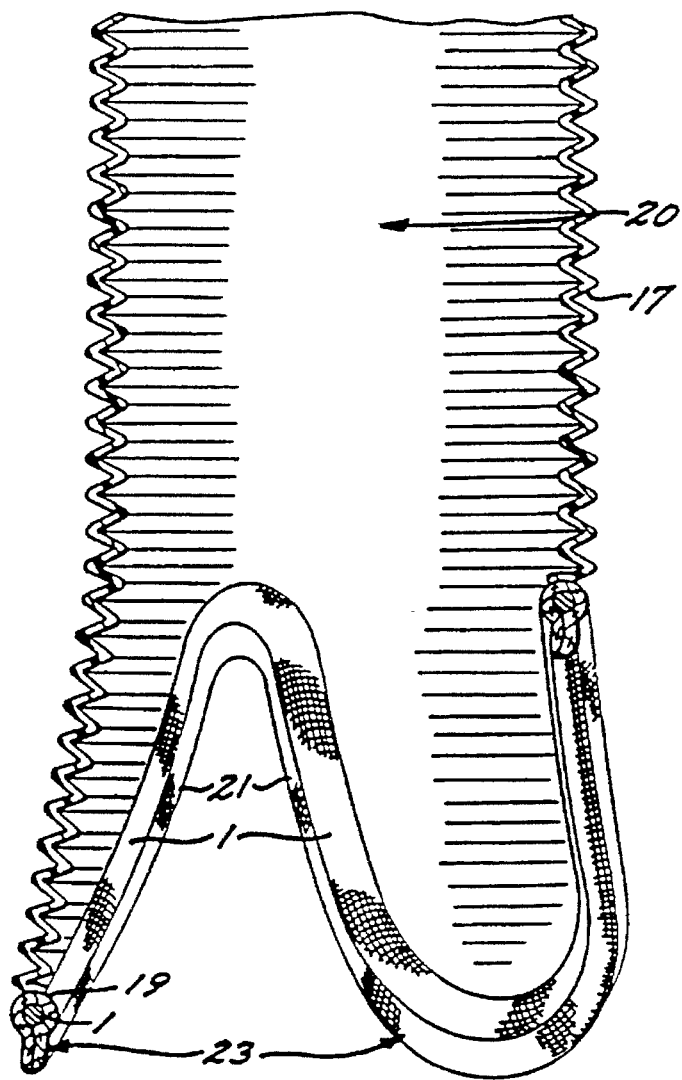
FIG. 14 is a cross-sectional view of the first preferred embodiment of the aortic valveless conduct, the cross-section being taken on lines 14—14 of FIG. 12.
Figure 13:
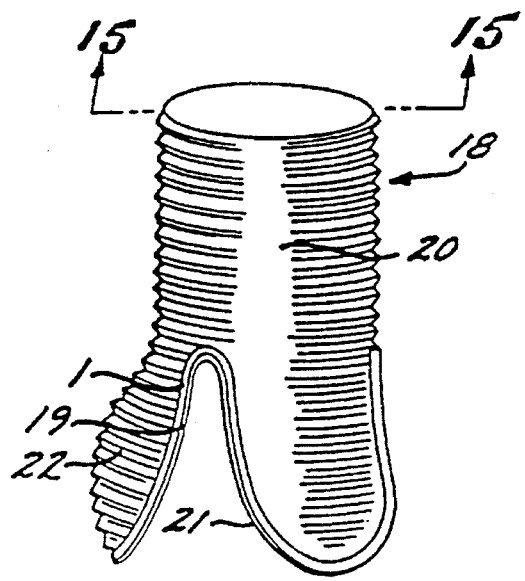
FIG. 13 is a perspective view of a second preferred embodiment of an aortic valveless conduit in accordance with the present invention, and incorporating the stent of the present invention and a vascular tube with sinuses of Valsalva.
Figure 15:
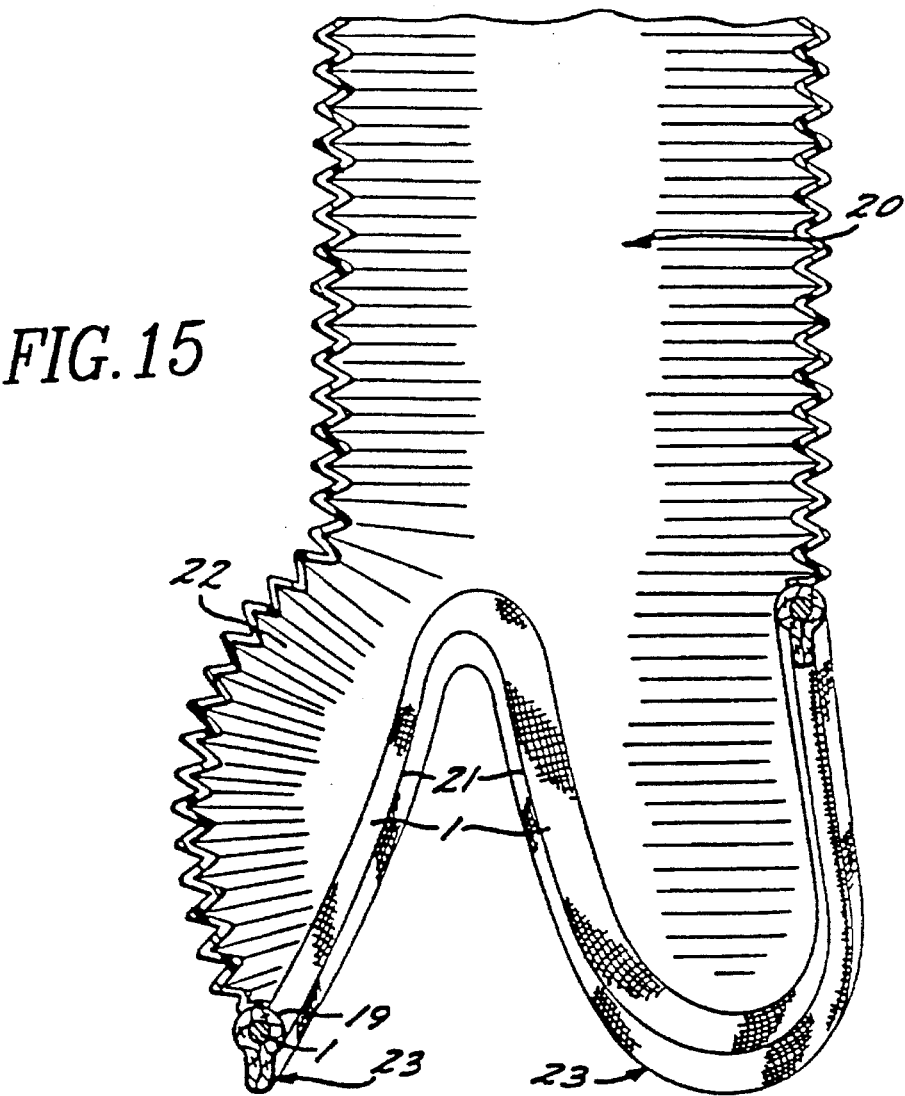
FIG. 15 is a cross-sectional view of the second preferred embodiment of the aortic valveless conduit, the cross-section being taken on lines 15—15 of FIG. 13.

Referring now to FIGS. 12 and 13, a first embodiment 17 and a second embodiment 18 of a valveless conduit are disclosed, each of which incorporates the novel annuloplasty ring or stent of the present invention. The valveless conduits are used when, in addition to remodelling of the aortic annulus, a portion of the ascending aorta must also be replaced because it is pathologically dilated.

As shown on FIGS. 12, 13, 14 and 15, the valveless conduit includes the stent 1 of the present invention, which is covered by biocompatible cloth or fabric 19. A cloth tube 20 of biocompatible material and of the type which is used in the state-of-the-art vascular substitutions is attached (by stitching or like means) to the stent 1. For this purpose, once end of the cloth tube 20 is formed (cut)in a scalloped fashion so as to conform to the configuration of the stent 1, and be attachable thereto. In accordance with the first preferred embodiment 17 of the valveless conduit, the cloth tube 20 attached to the stent 1, as is shown on FIGS. 12 and 14, has a substantially constant diameter. In accordance with the second preferred embodiment 18 of the valveless conduit, the cloth tube 20 is configured to form between each strut 21 of the stent 1 a sinus or bulge 22 so as to duplicate the naturally occurring three sinuses of the heart valve (Sinuses of Valsalva). A sewing ring or skirt 23 is also attached to the stent 1, or forms part of the cloth cover of the stent 1, to permit attachment by suturing of the valveless conduit to the remnants of the aortic wall of the patient. The sewing ring 23 requires no further detailed description here because it can be constructed in accordance with the state-of-the-art from the same materials which are used for sewing rings utilized in connection with the mechanical and tissue heart valves.

Bioabsorbable Material

As stated above, another aspect of the present invention is an absorbable stent or frame for a bioprosthetic heart valve which advantageously simplifies implantation, like stented bioprosthetic valves, while advantageously decreasing the long term stress on the biological portions of the valve and thereby increasing the valve's durability, like stentless bioprosthetic valves.

As used herein, "stent" and "frame" interchangeably refer to a mechanical structure used to support and give shape to the biological tissue portion of a bioprosthetic heart valve. The stent also serves as a structure used for attaching the bioprosthetic heart valve to the site of the excised natural valve.

In this aspect thereof, the present invention is a stent for a bioprosthetic heart valve that is made of absorbable material having a specific rate of absorption after implantation in a human or animal. The desired rate of absorption for the absorbable material is determined by two considerations. First, the structural integrity of the stent must remain long enough for the healing process to permanently affix the biological portions of the bioprosthetic heart valve to the site of implantation. Secondly, the stent should be substantially absorbed through naturally occurring host mechanisms at a fast enough rate to prevent long term stress on the biological portions of the valve with its attendant complications of mechanical failure and calcification.

The stent of this aspect of the present invention has a rate of absorption that is based on a number of factors. These factors include the quantity, shape and type of material that the stent comprises and, to some extent, the host-specific mechanisms involved in absorption. In general, a reasonable approximation of the absorption time can be made based on pre-implantation knowledge of quantity, shape and type of material factors.

In one preferred embodiment, a stent of the present invention is incorporated into a bioprosthetic heart valve for implantation into the aortic or pulmonary position. The stent is particularly suited for use in these positions because the biological tissue portion of the bioprosthetic heart valve can be affixed to the site of the excised natural valve in such a manner that no part of the bioprosthesis will depend on the stent for normal functioning at such time as the stent is substantially absorbed.

In another preferred embodiment, a stent of the present invention is incorporated into a bioprosthetic heart valve for implantation into a position other than the aortic or pulmonary position by utilizing substantially nonabsorbable materials in pads of the stent critical for long term function of the bioprosthetic valve in addition to substantially absorbable materials in parts of the stent not critical for long term function of the bioprosthetic valve.

Absorbable Stent

Figure 16D:
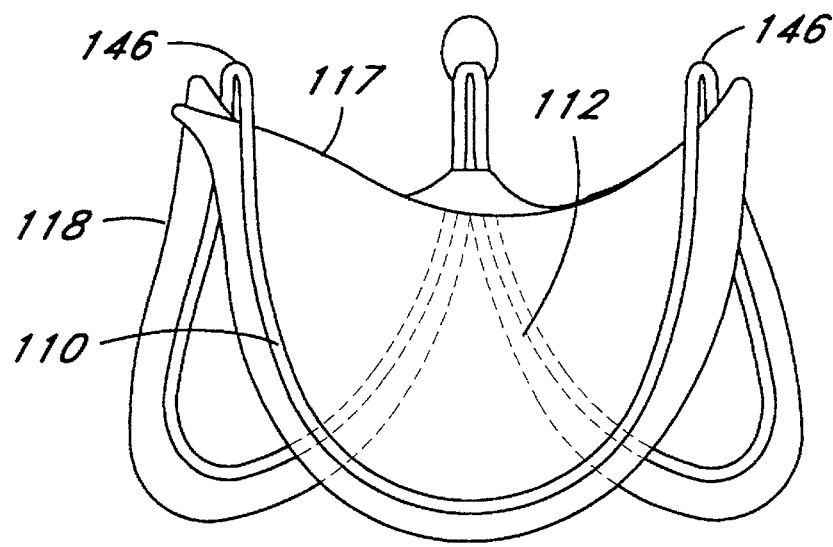

Referring now to FIG. 16A, there is illustrated a lateral perspective view of a substantially absorbable stent 110 for a bioprosthetic heart valve, according to one aspect of the present invention. The stent comprises a wire-like or filamentous structure formed into a shape corresponding closely to the "sigmoid" shape of the normal annulus of the aortic or pulmonary valves, the stent's curves 140 corresponding to the line of insertion of the aortic or pulmonary leaflets. The stent according to this preferred embodiment is designed for use with a bioprosthetic heart valve to be implanted into the aortic or pulmonary position, respectively.

Figure 17:
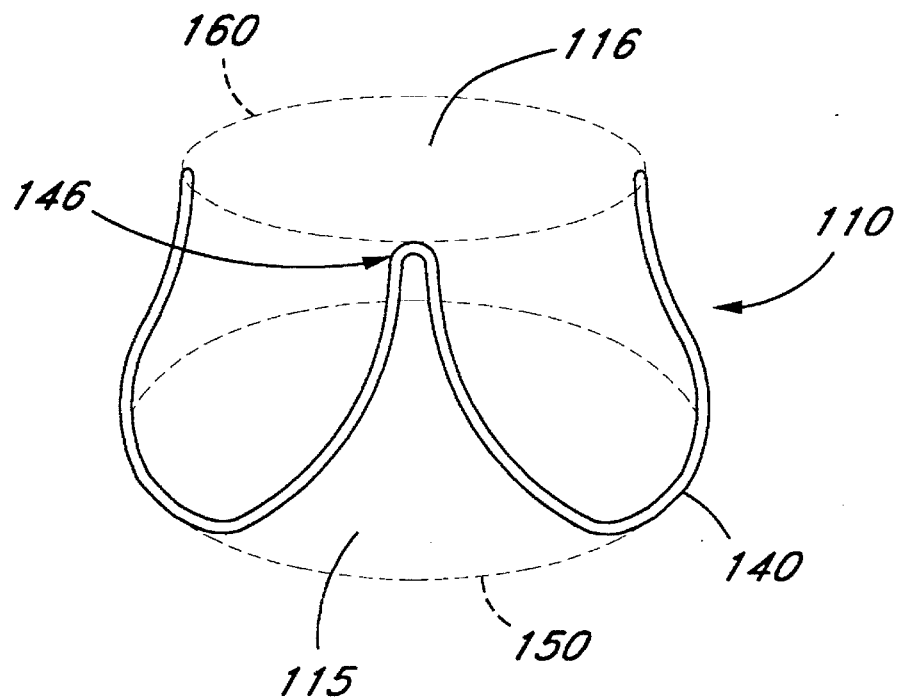
FIG. 17 is a perspective view of the preferred embodiment of the absorbable stent.

Referring to FIG. 17, the stent has a bottom or inflow end 115, and a top or outflow end 116. When viewed laterally, as shown in FIG. 16A, an absorbable stent according to one aspect of the present invention comprises three substantially identical curves 140 each having an inflow portion that is convex toward the inflow end 115 of stent 110. Each curve further comprises two ascending limbs 144 and each curve 140 is joined with the other curves at three equidistant commissural junctions 146 at the outflow end of the ascending limbs 144, corresponding to the commissural areas of the natural valve.

The stent 110 forms a generally circular structure. FIG. 17, illustrates two of the three curves 140 of absorbable stent 110. The phantom line 150 demonstrates the substantially circular nature of the inflow end of stent 110 formed by connecting the apices of the inflow portions of curves 140. Similarly, phantom line 160 demonstrates the substantially circular nature of the outflow end of stent 110 formed by the connecting the apices of the commissural junctions 146.

Figure 18:
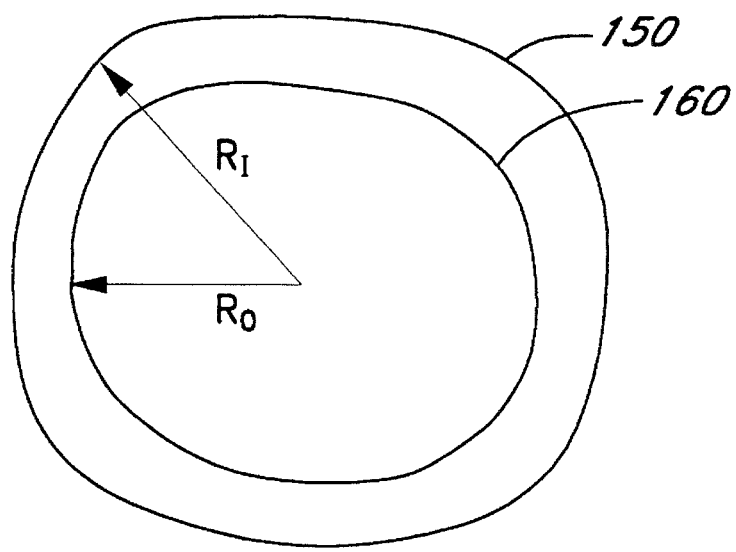
FIG. 18 is a top view of the preferred embodiment of the absorbable stent showing the difference between the "inflow" and "outflow" diameters.
Figure 19:
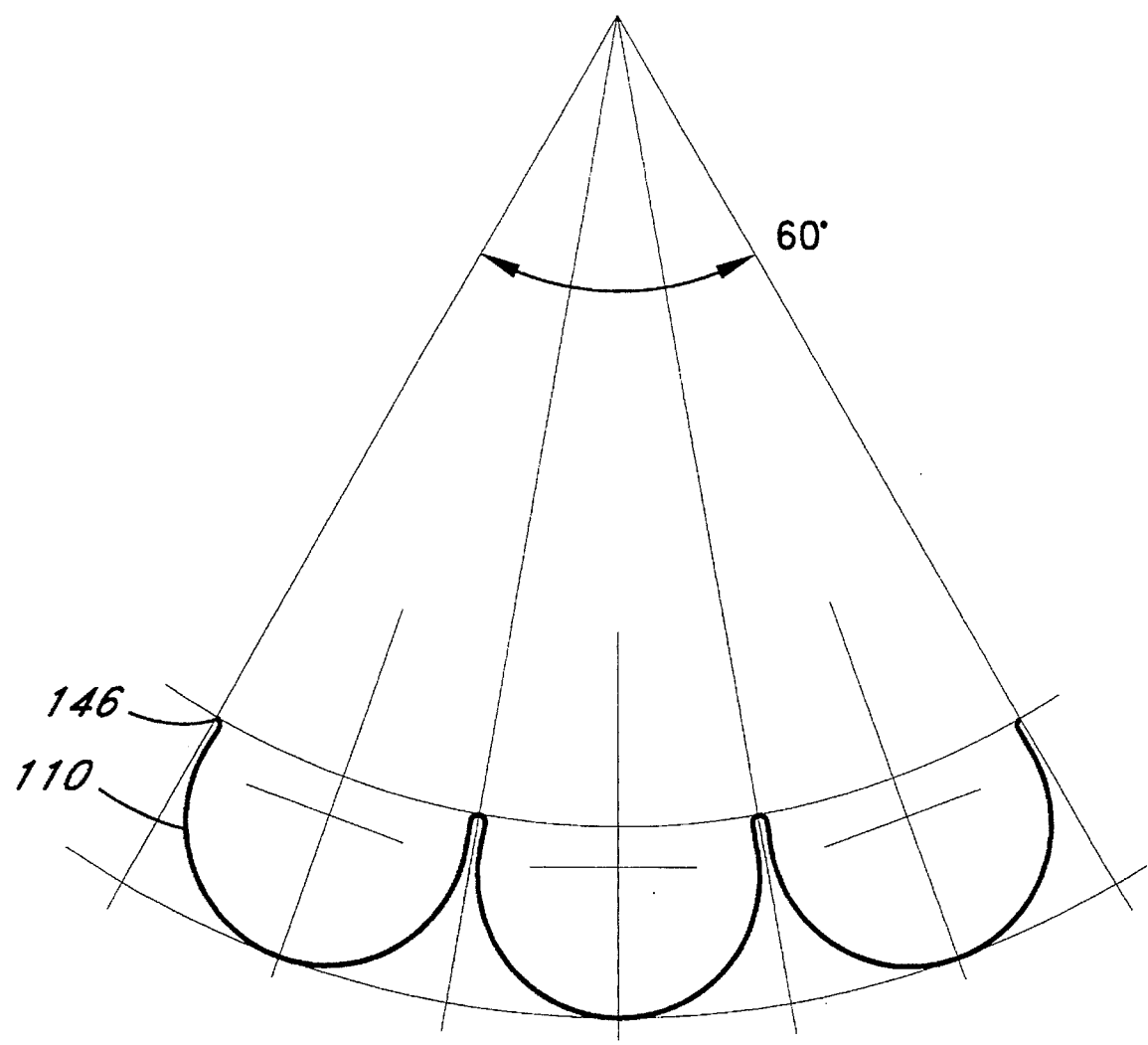
FIG. 19 is a lateral view of the preferred embodiment of the absorbable stent of the present invention, showing the stent as a flat pattern.

Referring now to FIG. 18, there is illustrated phantom lines 150 and 160 of FIG. 17 viewed from the top of the stent. It can be appreciated in this view that the outflow end of stent 110 has a smaller radius "$R_0$" than the radius "$R_1$" of the inflow end of stent 110, thus generally forming a truncated cone as illustrated in FIG. 17. The difference in the diameter between the inflow and outflow orifices of each absorbable stent is determined by the size of the specific stent.

As is shown in FIGS. 16–20, the stent 110 forms a convoluted ring. As the ascending limbs 144 of stent 110 approach the outflow orifice 116, they become straight and nearly parallel to each other until they join at commissural junction 146. The distance between adjacent ascending limbs 144, although variable, should not exceed approximately 2–3 millimeters at the level of the commissures.

Figure 20:
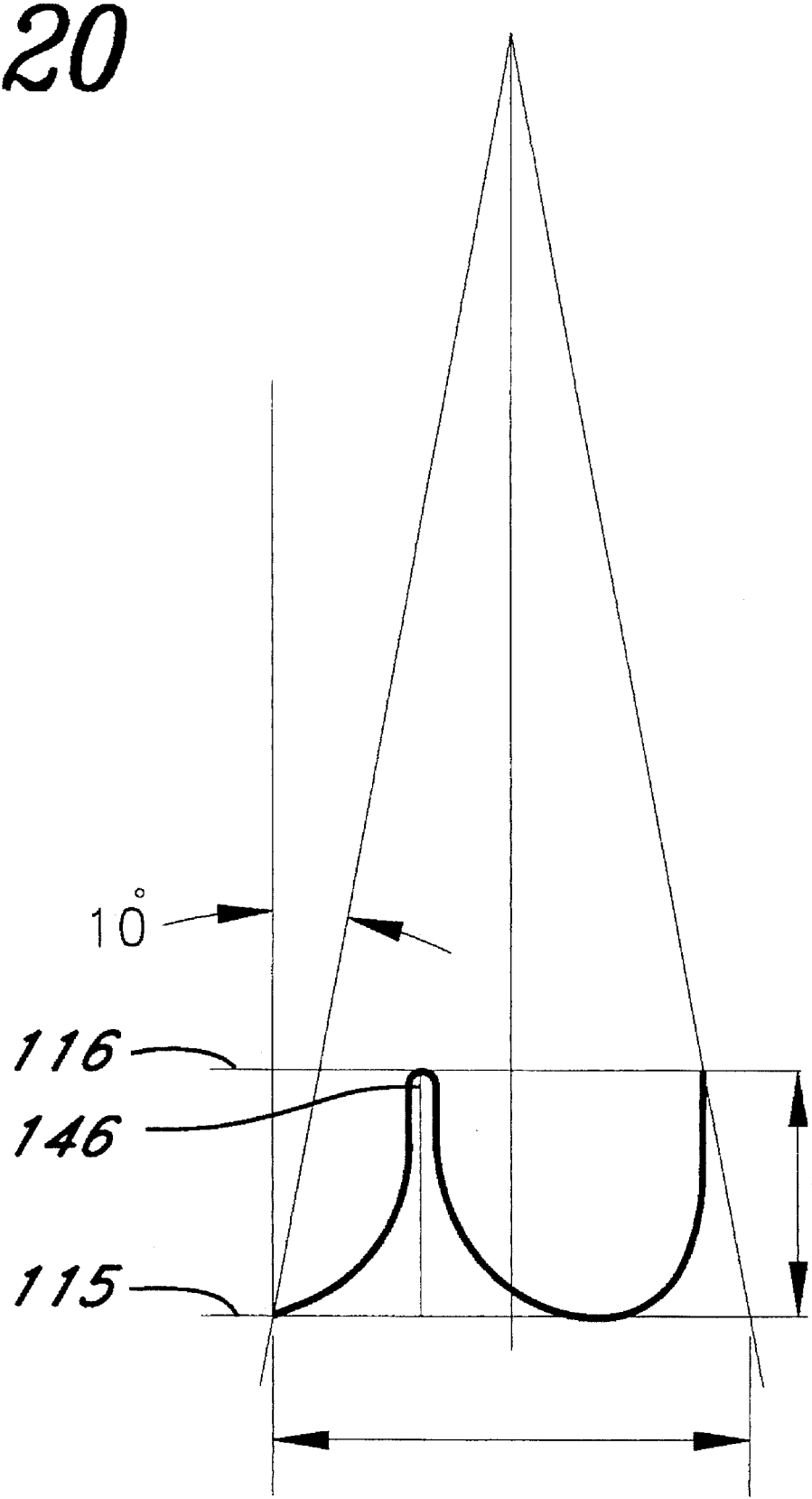
FIG. 20 is a lateral view of the preferred embodiment of the absorbable stent showing the relationship of its height to diameter and the difference between the "inflow" and "outflow" diameters.

The angle between the ascending limbs 144 and the vertical, as shown in FIG. 20, is approximately 10 degrees. This angle determines the differences between the inflow and outflow orifice diameters which depend on the size of the absorbable stent to be constructed. Given the normal size of the annulus of the human sigmoid valve, the range of inflow diameters will vary approximately between 10–35 millimeters. Those skilled in the art will recognize that the foregoing dimensions and proportions can be varied within certain limits.

The material used to manufacture the absorbable stent 110 must possess the following characteristics: (1) sufficient rigidity and strength to support a biological valve during the time of its surgical implantation; (2) biocompatibility; (3) predictable rate of absorption after implantation; and (4) predictable degree of inflammatory reaction and resulting residual fibrosis.

In a preferred embodiment, copolymers of polyglycolic acid (PGA) and polylactid (L-PLA) are used in the construction of the absorbable stent. Rods and tubes of these materials can be machined into the shape of stent 110 using techniques well known to those skilled in the art. Further, PGA and L-PLA have a predictable rate of disappearance. In a more preferred embodiment, PGA is used because of its 2–3 month rate of absorption compared to the rate of resorption of L-PLA, which is greater than one year.

A variety of other absorbable materials known to those skilled in the art can also be used in the construction of absorbable stent 110. For instance, copolymers of PGA and L-PLA combinations or polyhydroxybutyrate (PHB) or polyethylenes could be used. In addition, reconstituted collagen or soluble sugars could also be used.

Bioprosthetic Heart Valve Comprising An Absorbable Stent

In another preferred embodiment, there is provided a bioprosthetic heart valve for replacement of a native aortic or pulmonary valve, the bioprosthetic head valve comprising an absorbable stent 110 and biological tissue comprising a membrane. The membrane can be derived from pericardium, pleura, peritoneum, fascia lata or other biological membrane sources as is understood by those with skill in the art. The source of this biological membrane can be autologous, homologous, heterologous or xenogeneic. The membrane can also be derived from synthetic sources such as polyurethanes.

The bioprosthetic heart valve comprising an absorbable stent 110 and biological tissue comprising a membrane is constructed as follows. A source of biological membrane is selected and the membrane is harvested using methods known to those skilled in the art. The harvested membrane, such as autologous pericardium, is preferably treated using chemical and/or physical methods well known to those with skill in the art. In a preferred embodiment, autologous pericardium is treated with glutaraldehyde for approximately ten minutes. The harvested membrane 112 is cut into an appropriate shaped configuration such as that shown in FIG. 21, wherein three separate leaflets of membrane 112 are prepared. In a particularly preferred embodiment, the three cusps are joined together at two commissural areas 119 to form a single strip of biocompatible membrane as shown in FIG. 16B.

Figure 16E:
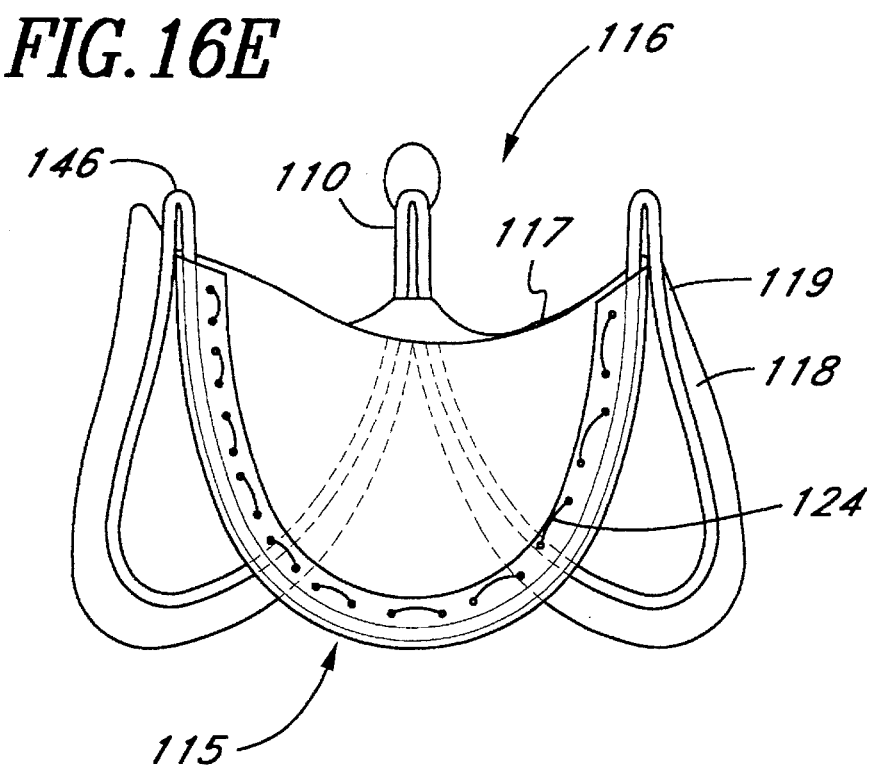
Figure 21:
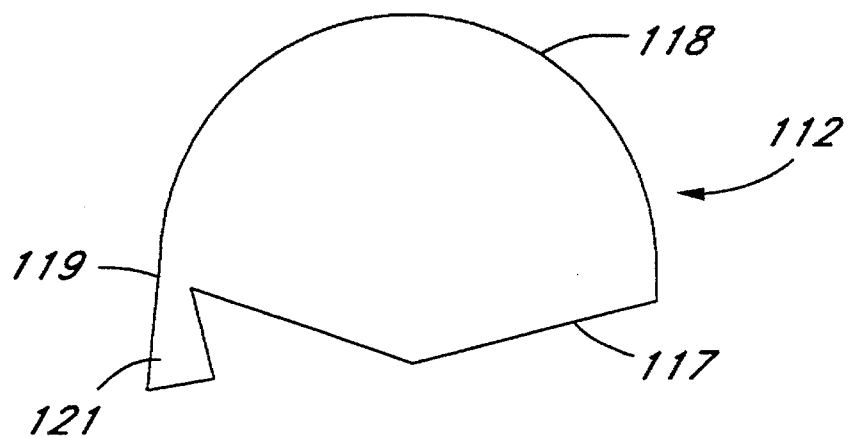
FIG. 21 is a plan view of one form of single leaflet of biocompatible membrane.
Figure 22:
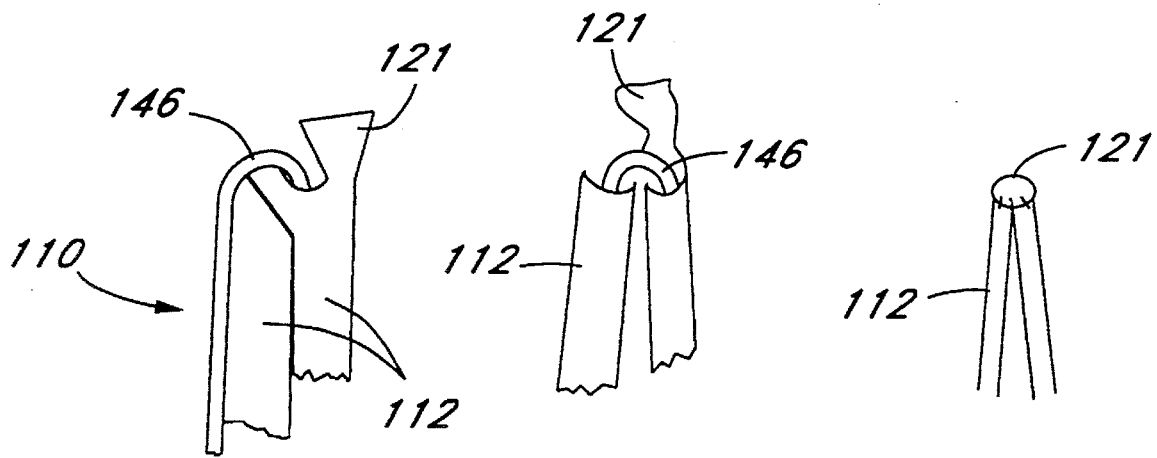
FIG. 22 depicts the construction of the bioprosthesis with a biological membrane at commissural level. In this preferred embodiment the two adjacent pericardial leaflets are being wrapped around the absorbable stent and a triangular piece of pericardium used to completely cover the uppermost part of the absorbable stent.

The size of each leaflet relates to the size of the bioprosthesis to be constructed. The shape and dimensions of membrane 112 used in the construction of the bioprosthetic valve are such that, when affixed to absorbable stent 110, the three free edges 117 can come into contact with each other to close the blood flow path defined by absorbable stent 110, while the commissural areas 119 and the insertion lines 118 cover absorbable stent 110 once membrane 112 is sutured around stent 110 as illustrated in FIG. 16E. In addition, each leaflet has a generally triangular protrusion 121 at the level of one commissural area 119 as illustrated in FIG. 21. Protrusion 121 is used to cover the uppermost portion of absorbable stent 110 as shown in FIG. 22.

Referring now to FIGS. 16C–E and 23, there is illustrated one preferred method of affixing membrane 112 to stent 110. As shown, membrane 112 is wrapped around the inner or central aspect of the stent so that, when the wrapping reaches the commissural junctions 146, the two lobes are passed through the small gap between the two adjacent ascending limbs 144 of the stent. The membrane is then fixed to the stent by any of a number of techniques known to those with skill in the art, including suturing and gluing. In order to avoid embolization when the stent starts being absorbed, the remaining uncovered portion of absorbable stent 110 is covered as illustrated in FIG. 22 whereby the roughly triangular protrusion 121 of the leaflet is brought back over the uppermost portion of absorbable stent 110 where it is affixed to both upper extremities of free edges 117.

Figure 23:
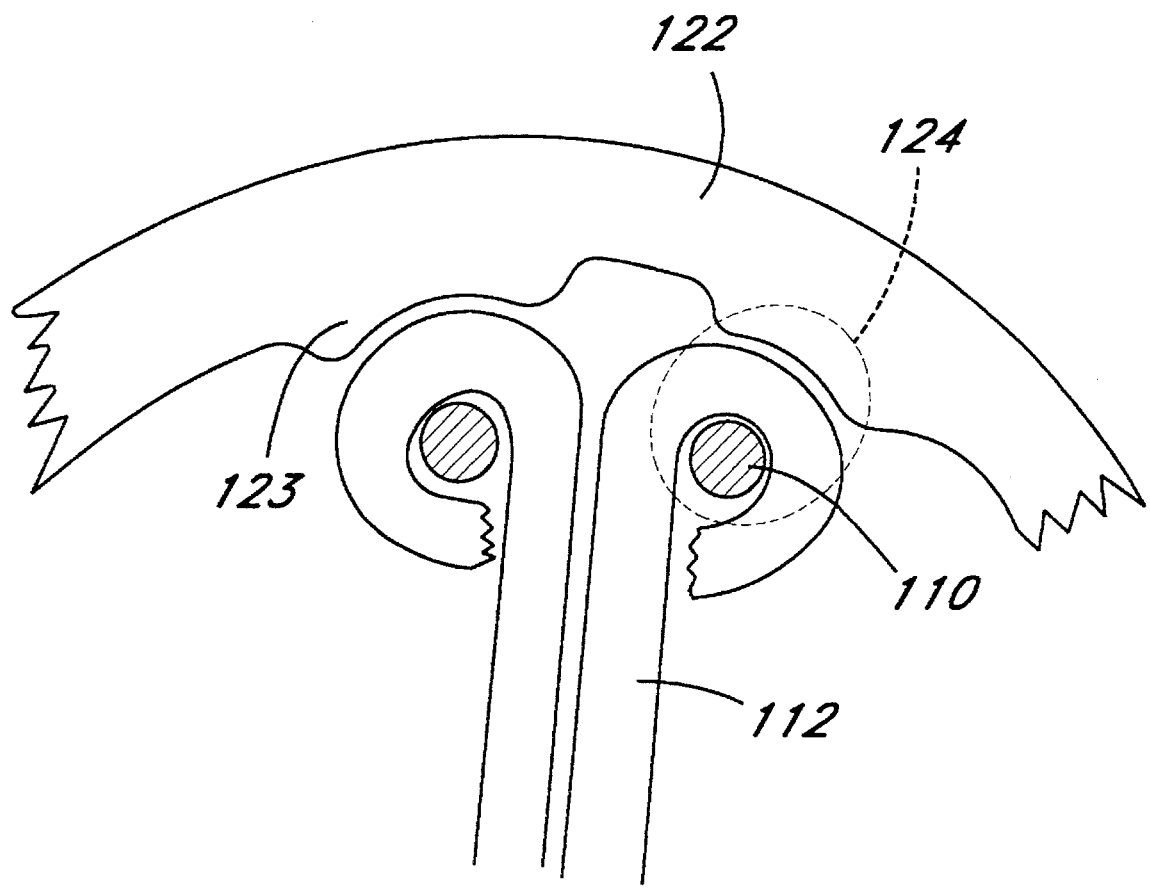
FIG. 23 is a cross-sectional view of the bioprosthesis made of pericardium (in the closed position) and absorbable stent at the level of one commissure. The aortic valve remnant of the patient is represented as well as the surgical suturing of the bioprosthesis to the aortic annulus.
Figure 25:
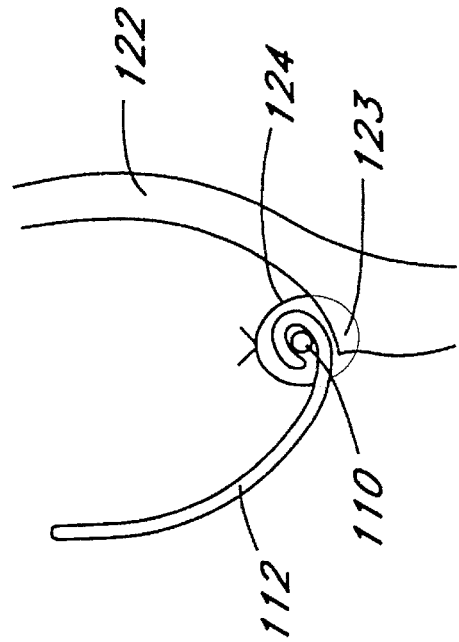
FIG. 25 is a diagram of the bioprosthesis made of biological membrane on the absorbable stent of the present invention being sutured to the aortic annulus of a patient.
Figure 24:
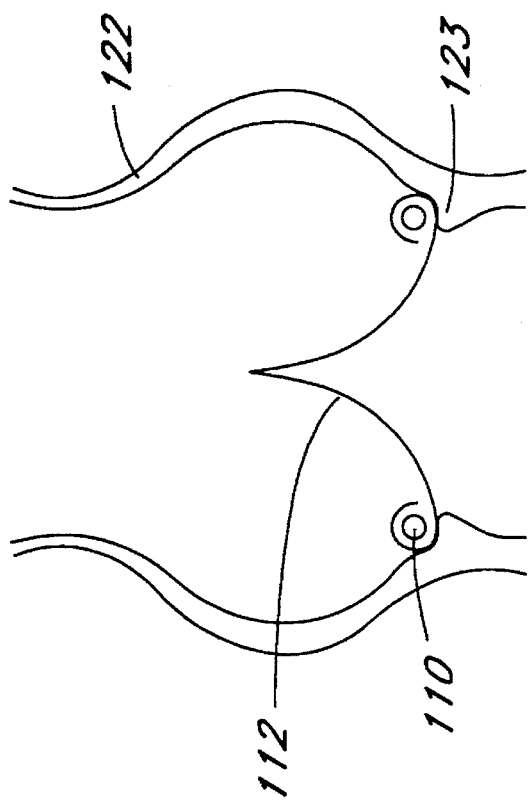
FIG. 24 is a diagram of the bioprosthesis made with biological membrane on the absorbable stent of the present invention, placed in the aortic annulus of a patient.

The bioprosthesis comprising the absorbable stent 110 and biological membrane 112 is implanted into the aortic or pulmonary annulus of the patient as illustrated in FIG. 23 where the aortic or pulmonary wall is diagrammatically represented as reference numeral 122, together with the remnant of excised diseased valve 123. After excision of the diseased native valve, the bioprosthesis is implanted into the aortic or pulmonary annulus using techniques well known to those skilled in the art. In particular, a preferred method of implantation comprises suturing the membrane and absorbable stent together to the sigmoid valve annulus at the site of the excised native valve utilizing either interrupted or continuous suture 124 as shown diagrammatically in FIGS. 23 and 25. Proline or polypropylene suture is preferably used. The healing process of the patient anchors the membrane in place while progressively absorbing the stent. This process results in the substantial or total disappearance of the stent leaving a stentless bioprosthesis.

Using the method described above, the bioprosthesis comprising the absorbable stent 110 and biological membrane 112 has been successfully implanted into a number of sheep. In these experiments, the absorbable stents were constructed using L-PLA or PGA. The biological membrane was derived from autologous pericardium. Successful results were indicated by postoperative weight gain. In addition, bioprosthetic valve function was assessed using echocardiography and found to be within acceptable ranges in the typical postoperative animal surviving surgery. Valve function was also assessed by hemodynamic studies, such as by measuring the pressure gradient across the bioprosthetic valve. Theses studies were also indicative of successful postoperative valve function.

Yet another preferred embodiment of the present invention comprises the use of absorbable stent 110 together with an aortic or pulmonary sigmoid valve of human or animal origin. The bioprosthetic valve is constructed as follows. First, a source of biological material is selected. Next, the valve serving as the source of the biological tissue is harvested such that the three valve leaflets are preserved together with a small portion of adjacent vessel wall, the vessel wall remnant 126. This technique is well known to those skilled in the art. See, e.g., Duran & Gunning, Lancet 1962, 2:488; or Barrat-Boyes, Thorax 1964, 19:131.

Figure 26:
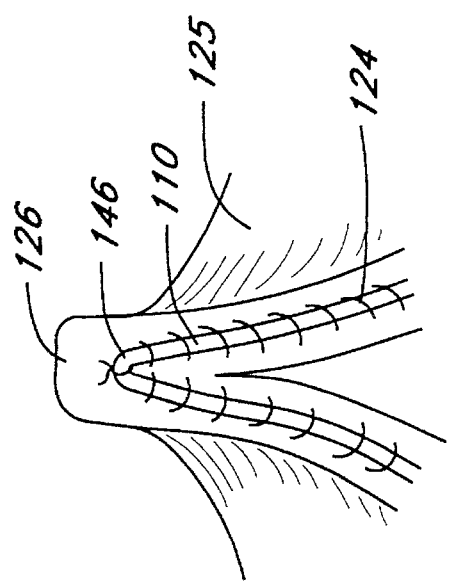
FIG. 26 shows a diagrammatic form, a partial view of the outer or adventitial aspect of a human or animal sigmoid valve at the level of one commissure. The absorbable stent is shown in place held with a continuous suture.

Next, an absorbable stent 110 is provided. The appropriate size of the absorbable stent is selected to be approximately two millimeters wider in diameter than the dissected sigmoid valve of human or animal origin. As illustrated in FIG. 26, the harvested valve 125 is placed inside the absorbable stent 110 so that each part of the stent corresponds to each anatomical part of the sigmoid valve. The stent is then held in place with suture 124 making sure that a rim of aortic or pulmonary wall remnant 126 protrudes a few millimeters beyond stent 110. The stent can also be held in place by gluing or other means well known to those of skill in the art.

Surgical implantation of this stented autologous, homologous (cadaveric) or heterologous (animal) aortic or pulmonary sigmoid valve is highly simplified because of the presence of stent 110, which is a rigid structure that maintains the normal geometry of the valve and directs the surgeon in its suturing.

Figure 28:
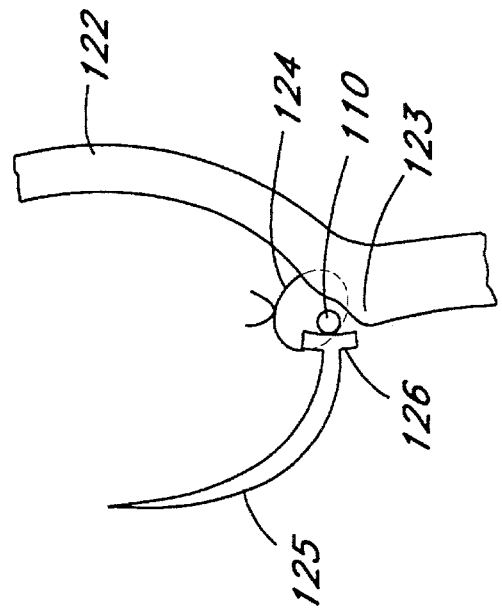
FIG. 28 shows in a diagrammatic form, a cross section of a human or animal sigmoid valve with the absorbable stent of the present invention sutured to the aortic annulus of a patient.
Figure 27:
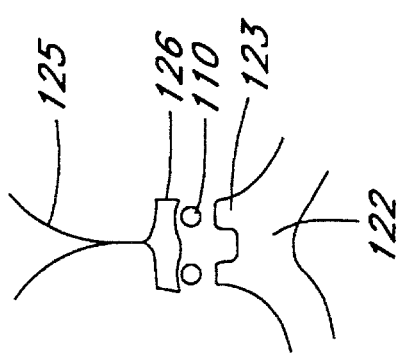
FIG. 27 shows in a diagrammatic form, a cross section of a human or animal aortic valve and absorbable stent of the present invention placed next to the remnant of the excised sigmoid valve of a patient.

FIG. 27 diagrammatically illustrates a cross-section of the patient's aortic wall 122, the remnant of excised sigmoid valve 123, the absorbable stent 110, and the vessel wall remnant 126 and cusps of harvested sigmoid valve 125 to be implanted at a level close to one commissure. The bioprosthesis is implanted according to methods well known in the art. FIG. 28 diagrammatically illustrates one method of implantation, wherein the vessel wall remnant 126 together with the stent 110 are sutured to the annulus at the site of the excised native valve using either interrupted or continuous suture 124.

Several modifications of the above-described novel annuloplasty prosthesis and of the associated part and processes may become readily apparent to those skilled in the art in light of the above disclosure. Therefore, the scope of the present invention should be interpreted solely from the following claims, as such claims are read in light of the disclosure.

What is claimed is:

1. A bioprosthetic heart valve comprising:

a stent defining a blood flow path, said stent being formed at least partially of substantially bioabsorbable material; and a plurality of leaflets, each of said leaflets having an outer edge and an inner edge, each of said inner edges being affixed to said stent, said outer edges adapted to come into contact with each other to close the blood flow path defined by said stent.

2. The bioprosthetic heart valve of claim 1, wherein the leaflets comprise a biological material.

3. The bioprosthetic heart valve of claim 2, wherein the biological material comprises a substantial portion of a human cadaveric heart valve.

4. The bioprosthetic heart valve of claim 2, wherein the biological material comprises a substantial portion of a xenogeneic animal heart valve.

5. The bioprosthetic heart valve of claim 2, wherein the biological material is selected from the group consisting of pericardium, pleura, peritoneum, fascia lata and a combination of any of the foregoing.

6. The bioprosthetic heart valve of claim 2, wherein the biological material is selected from the group consisting of xenogeneic tissue, homologous tissue, autologous tissue and a combination of any of the foregoing.

7. The bioprosthetic heart valve of claim 1, wherein the stent is configured from a closed filament having an inflow end and outflow end, wherein the filament has a plurality of convexities oriented toward the inflow end and a plurality of peaks oriented toward the outflow end.

* * * * *